(12) United States Patent
Choy et al.

(10) Patent No.: US 9,474,853 B2
(45) Date of Patent: Oct. 25, 2016

(54) IMPLANTABLE DEVICE FOR DRUG DELIVERY OPERATED BY MAGNETIC FORCE

(71) Applicant: SNU R&DB Foundation, Seoul (KR)

(72) Inventors: Young Bin Choy, Seongnam-si (KR); Seung Ho Lee, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 377 days.

(21) Appl. No.: 14/303,441

(22) Filed: Jun. 12, 2014

(65) Prior Publication Data

US 2014/0371727 A1    Dec. 18, 2014

(30) Foreign Application Priority Data

Jun. 17, 2013 (KR) .......................... 10-2013-0068819

(51) Int. Cl.
*A61K 9/22* (2006.01)
*A61M 5/145* (2006.01)
*A61M 5/142* (2006.01)

(52) U.S. Cl.
CPC ....... *A61M 5/1452* (2013.01); *A61M 5/14276* (2013.01); *A61M 2005/14506* (2013.01); *A61M 2205/8287* (2013.01)

(58) Field of Classification Search
CPC .......... A61M 2005/14506; A61M 2205/8287; A61M 5/14276; A61M 5/1452; A61M 5/16804
USPC ...................................... 604/891.1
See application file for complete search history.

(56) References Cited

U.S. PATENT DOCUMENTS

| | | | |
|---|---|---|---|
| 7,288,085 B2 * | 10/2007 | Olsen ................ | A61M 5/14276 604/151 |
| 2009/0209945 A1 * | 8/2009 | Lobl ................. | A61M 5/14224 604/891.1 |
| 2012/0059349 A1 * | 3/2012 | Kuo .................... | A61M 5/1407 604/500 |

* cited by examiner

Primary Examiner — Jason Flick
(74) Attorney, Agent, or Firm — Stein IP, LLC (57) ABSTRACT

Disclosed is an implantable device for drug delivery operated by a magnetic force. The device is provided with a body member and an external magnetic controller which is able to move some of the parts in the body member so that the drug inside the body member can be delivered to a site of interest of the animal body without the extra power source.

7 Claims, 11 Drawing Sheets

| Magnet | Distance (mm) | Theoretical F (N) |
|---|---|---|
| M₂ ←→ M₃ | 3/5 | 7.65/4.83 |
| M₁ →← M₃ | 10 | 0.002 |
| M₁ ←→ M₂ | 1.8 | 4.53 |

|      | 1 Actuation      | 3 Actuations     |
|------|------------------|------------------|
| 1MDD | 60.98 ± 2.52 μg  | 176.51 ± 2.92 μg |
| 2MDD | 87.93 ± 1.62 μg  | 258.58 ± 6.32 μg |
| 3MDD | 123.1 ± 1.83 μg  | 365.15 ± 12.4 μg |

| | day | ng/ml |
|---|---|---|
| 3MDD 3 Actuation (365 µg) | 5 | 218.1222 |
| S.C injection (365 µg) | 5 | 221.0273 |

FIG. 6

IMPLANTABLE DEVICE FOR DRUG DELIVERY OPERATED BY MAGNETIC FORCE

CROSS-REFERENCE TO RELATED APPLICATIONS

This present application claims the benefit of Korean Patent Application No. 10-2013-0068819, filed Jun. 17, 2013 in the Korean Intellectual Property Office, disclosure of which is incorporated herein by reference.

BACKGROUND OF THE INVENTION

1. Field of the Invention

The present disclosure generally relates to implantable drug delivery systems and methods of using thereof.

2. Description of the Related Art

Patients with chronic disease such as cancer, AIDS, diabetes or chronic pain often require a long term and/or continuous treatment with medication. For this, drug therapy or pharmacotherapy, which is the treatment of disease through the administration of drugs, is widely employed. Particularly, chronotherapy is a treatment method in which in vivo drug availability is timed to match the rhythms of disease in order to optimize therapeutic outcomes and minimize side effects. The desirable regimen for pain relief drug or macromolecular drugs, such as insulin or growth hormones is also their delivery in a timed manner. Drug delivery system which is commonly used for timed delivery includes oral delivery systems, injection systems and implantable devices and the like.

However, oral delivery systems have some drawbacks such as low bioavailability and severe side effects due to the inactivation or degradation of the drug in the gastrointestinal passage. Injection systems, which are known for its high efficiency, also have some problems associated with the increased number of injections in order to keep the concentration of a drug at a certain level, which results in the patient inconvenience and distress. The drawbacks associated with implantable devices that can be divided active and passive types, are such that the passive types, which are designed for continuous, sustained release of a drug, is generally not suitable for the patients' driven drug delivery due to the lack of external control of drug release, and the active types are usually equipped with a controller operated by a battery to address the problem associated with the passive system, which, however, causes an additional problem due to the limited lifetime of battery, thereby needing a secondary surgery for device replacement and results in a device that is not suitable for the implantation due to the increased size by the battery.

US Patent Publication No. 2009-0209945 relates to valveless impedance pump drug delivery system and discloses a system in which a drug is released by a pressure wave reflection generated inside an elastic tube by applying the tube magnetic force and thus the system requires devices to generate and to control the impudence, which leads to a complex device with increased size.

US Patent Publication No. 2009-0209945 relates to magnetically-controllable delivery system for therapeutic agents and discloses a system wherein the agent bound to magnetizable nanoparticles is controllably delivered through a magnetizable object implanted in the body through magnetic gradient generated in the system. However this has some drawbacks that it requires a drug that is associated with magnetizable nanoparticles.

As such, there exist needs for the development of implantable drug delivery system based on magnetic force, which is small sized without battery, and internal hardware to control the device yet is able to finely control the dose of drug and the time of administration.

SUMMARY OF THE INVENTION

One aspect of the invention provides an implantable device for drug delivery operated by magnetic force. The device comprises: a chamber comprising a top end and a bottom end; the chamber further comprising at least one septum for charging a drug into the device and at least one outlet for discharging a drug from the device, the septum being formed on the top end of the chamber and the outlet being formed on the bottom end of the chamber; an actuator located within the chamber, the actuator comprising a cylinder and a piston; the cylinder comprising at least one inlet formed on the side thereof and a first flange protruding outwardly from the outer surface of the cylinder; the first flange formed on the end of the cylinder that is closer to the top end of the chamber and being configured to abut the inner surface of the chamber; the piston being located inside of the cylinder and comprising an end cap; the end cap covering the end of the piston that is located closer to the top end of the chamber such that the end cap is interposed between the first flange and the top end of the chamber and being configured to abut the inner surface of the chamber; and a drug reservoir formed in a space within the chamber that is not occupied by the actuator; and an external controller for supplying a initiating magnetic force to the device, wherein at least one of the first flange and the end cap is formed of a magnetic material or a material that is responsive to a magnetic force such that they are positioned close to each other when the initiating magnetic force is not applied or removed after it being applied.

The present device is composed of two parts which are not physically connected to each other. In this context all the structures or the elements except the external controller constitutes a first part which comprises a chamber, an actuator and a drug reservoir, which may be referred to as a body member and the external controller constitutes a second part.

In the device, the operation thereof is initiated by applying the initiating magnetic force $M3$ to the top end of the chamber, thus pulling the piston upward and opening the inlet through which the drug is introduced to the cylinder followed by a subsequent release and delivery of the drug through the outlet to a site of the body where the device is implanted, wherein the first flange has a magnetic force $M1$ and the end cap has a magnetic force $M2$, and the $M1$, $M2$ and $M3$ meet the following condition for the proper operation: $M2-M3>M2-M1$ for the introduction of the drug to the cylinder through the inlet; and $M2-M3<M2-M1$ for the release of the drug to the site of the body where the device is implanted through the outlet.

In the foregoing device, the ratio of the total area of the outlet to that of the inlet is preferably controlled for proper operation of the device. In one embodiment the ratio is above 1:1 (total area of the outlet: total are of the inlet), particularly in the range of 1:1 to about 1:50, for example 1:40, 1:30, 1:20 and 1:10 without limitation.

In the foregoing device, the amount of a drug released from the drug reservoir per actuation can be controlled by the size and/or number of the outlet, the ratio of the total area of the inlet and the outlet, or the volume of the cylinder or the combination thereof.

Other aspect of the invention provides a method of delivering a drug using the foregoing device. The method includes the steps of implementing the device at a site of interest of the subject and actuating the device to deliver the drug in an amount sufficient to treat or a disease of interest or relives a symptom of interest.

It is an advantage of the present device that the device is operated by magnetic force and does not require extra power source such as battery so that it can be manufactured in relatively small size which reduces the manufacturing cost of the device and improves the user convenience. Further it can obviate the trouble of a secondary surgery that is often required for replacing the device with battery. Thus the present device may be used for semi-permanently.

It is another advantage of the present device that the user convenience is further improved the number and amount of drug administered can be finely controlled by a simple application of a magnetic force.

It is still another advantage of the present device that the device is provided with a drug reservoir for recharging a drug when need thus it is suitable for treating disease that requires a medication treatment for extend period of time The foregoing summary is illustrative only and is not intended to be in any way limiting. Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 5 A is a graph showing the accumulated amount of 5-FU released with the increased number of actuation in which 5-FU was released with an interval of 15 minutes. Each line of the graph corresponds to the result using a device with 1, 2 or 3 MDD respectively.

In FIGS. 5A to 5C, each point at the graphs represents data from 3 independent experiments and for the actuation, and pulsed magnetic field of 4000G was applied for each actuation.

DETAILED DESCRIPTION OF THE EMBODIMENTS

As describe above, the present device has been developed to overcome the problems associated with prior art systems. The present device can be conveniently used for drug delivery as implanted systems for treating chronic disease, condition or state that requires medication therapy over extended period of time, for example cancer, diabetes, chronic pain, AIDS and contraception and the like.

Accordingly various devices of various exemplary aspect and embodiments of this invention are designed to deliver a drug as an implanted system that is small sized lacking power supply and electronic hardware and also with which the user can finely control the amount and time of drug administered. To this end, various devices of the present disclosure are provided with elements that are operated through and/or by the application of a magnetic force. Reference will now be made in greater detail to the present embodiments, examples of which are illustrated in the accompanying drawings. Wherever possible, the same reference numerals will be used throughout the drawings and the description and the description to refer to the same or like parts.

Hereinafter, exemplary aspects of the disclosure will be described with reference to the accompanying drawings through which like elements are referenced by like numbers. In describing the invention, details on the structure or function of related arts are omitted if they may obscure the subject of the invention.

Terms in the description are defined considering functions of elements of the invention, so that the terms must be construed with reference to the contents of the present disclosure as a whole because such terms can be differently defined according to the intent of people skilled in their arts or customs.

The present invention relates to an implantable drug delivery system utilizing magnetic forces. In one aspect, the present device is for implanting into animal and comprises: a chamber (100) comprising a top end and a bottom end, the chamber further comprising at least one outlet (106) formed on the bottom end (104) of the chamber and at least one septum (108) for charging a drug formed on the top end (102) of the chamber; an actuator (200) that is located inside the chamber, the actuator comprising a cylinder (202) and a piston (208) located inside the cylinder, the cylinder comprising at least one inlets (206) formed on a side of the cylinder and a first flange (204) protruding outwardly from an outer surface of the cylinder, the first flange formed on the end of the cylinder that is closed to the top end of the chamber, the piston (208) comprising an end cap, the end cap covering an end of the piston that is adjacent to the top end (102) of the chamber and formed such that it tightly contacts with an inner surface of the chamber, and a drug reservoir (212), formed in a space within the chamber (100) that is not occupied by the actuator (200); and an external controller (300) for supplying a initiating magnetic force to the device, wherein at least one of the first flange and the end cap is formed of a magnetic material or a material that is responsive to a magnetic force such that they adhere to each other when the initiating magnetic force is not applied.

Figure 1A:
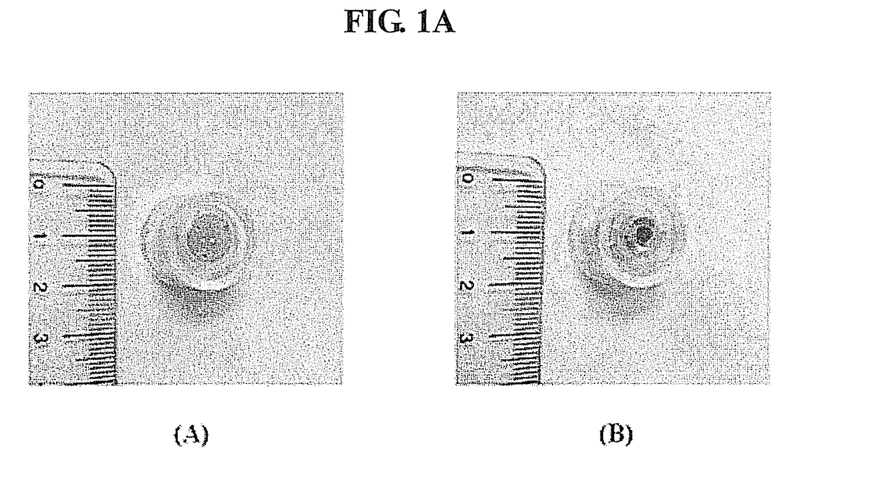
FIG. 1A is an image showing a device according one exemplary embodiment of the present disclosure, in which A represents a top end in which a septum is provided and B represents a bottom end in which an outlet is provided.
Figure 1B:
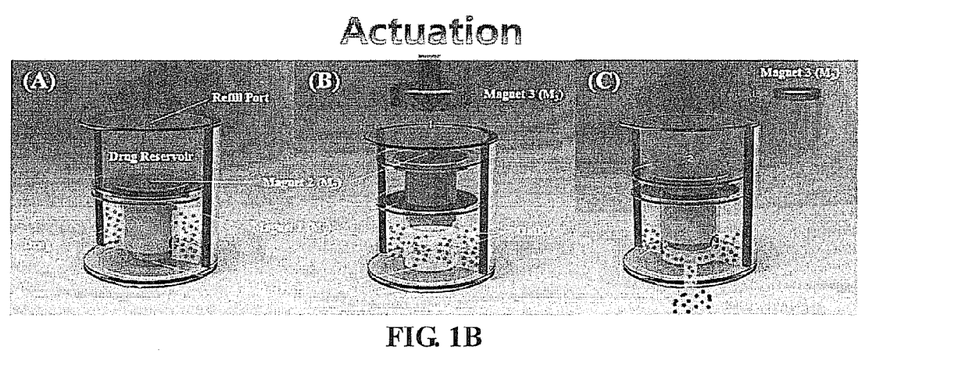
FIG. 1B is a schematic illustration showing a process of drug delivery using one exemplary device of the present disclosure.
Figure 2A:
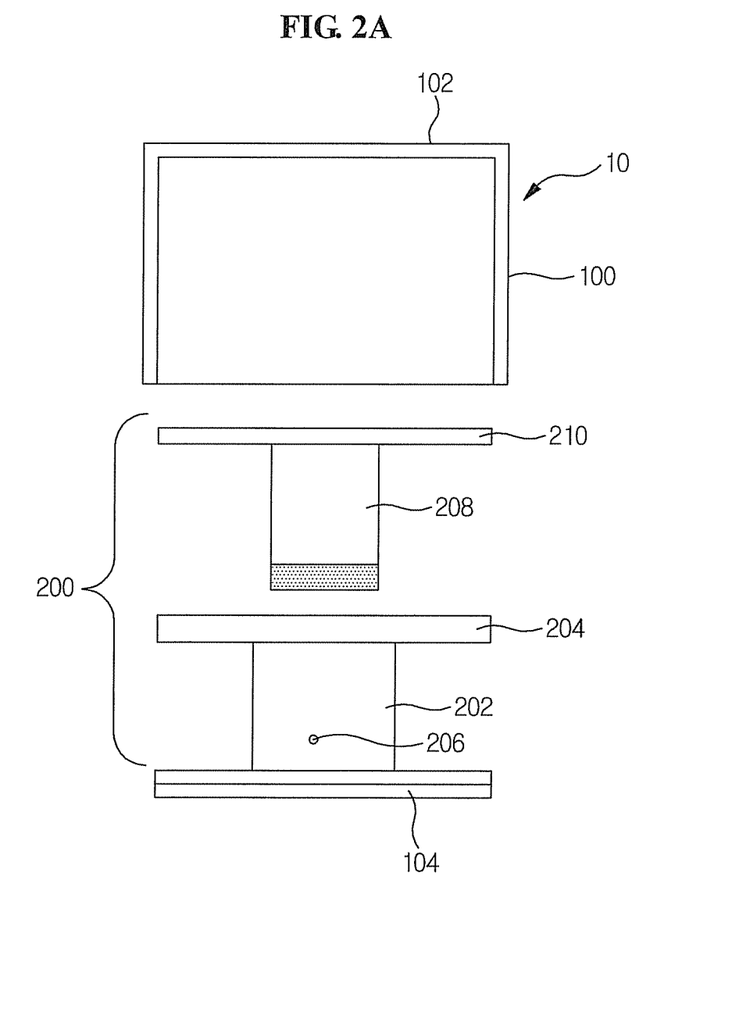
FIG. 2A is an exploded cross-sectional view showing each element constituting a device according to one exemplary embodiment of the present disclosure.

FIG. 1A is an image showing a device according one exemplary embodiment of the present disclosure, in which A represents a top end in which a septum is provided and B represents a bottom end in which an outlet is provided and FIG. 1B is a schematic illustration showing a process of drug delivery using one exemplary device of the present disclosure in which A represents a stand-by state. B represents a actuation state initiated by the application of a magnetic field and C represents a state when the magnetic force is removed. FIG. 2A is an exploded cross-sectional view and FIG. 2B and 2C are exploded perspective views showing each element constituting a device according to one exemplary embodiment of the present disclosure.

As shown in FIG. 1B, the present device is an implantable drug delivery system based on magnetic force, and when the device is ready for delivery, i.e., in a stand-by state, it is configured to be blocked from the outside environment. And then only by the application of a magnetic field, a piston 208 of an actuator 200 of the present device is pulled upward, which makes a space inside a cylinder 202 and allows a drug in a reservoir 212 to be introduced and move into the space of the cylinder through an inlet(s) 206. When the external force is removed, the piston 208 returns to the position in a stand-by state, by which the inlet(s) 206 are closed and thus blocking the flow of a drug into the chamber, and the drug is discharged out of the cylinder and is delivered to a site of the body where the device is implanted through an outlet 106 formed on the bottom end of the device. In this context the present devices may be referred as an on-off type.

Figure 2B:
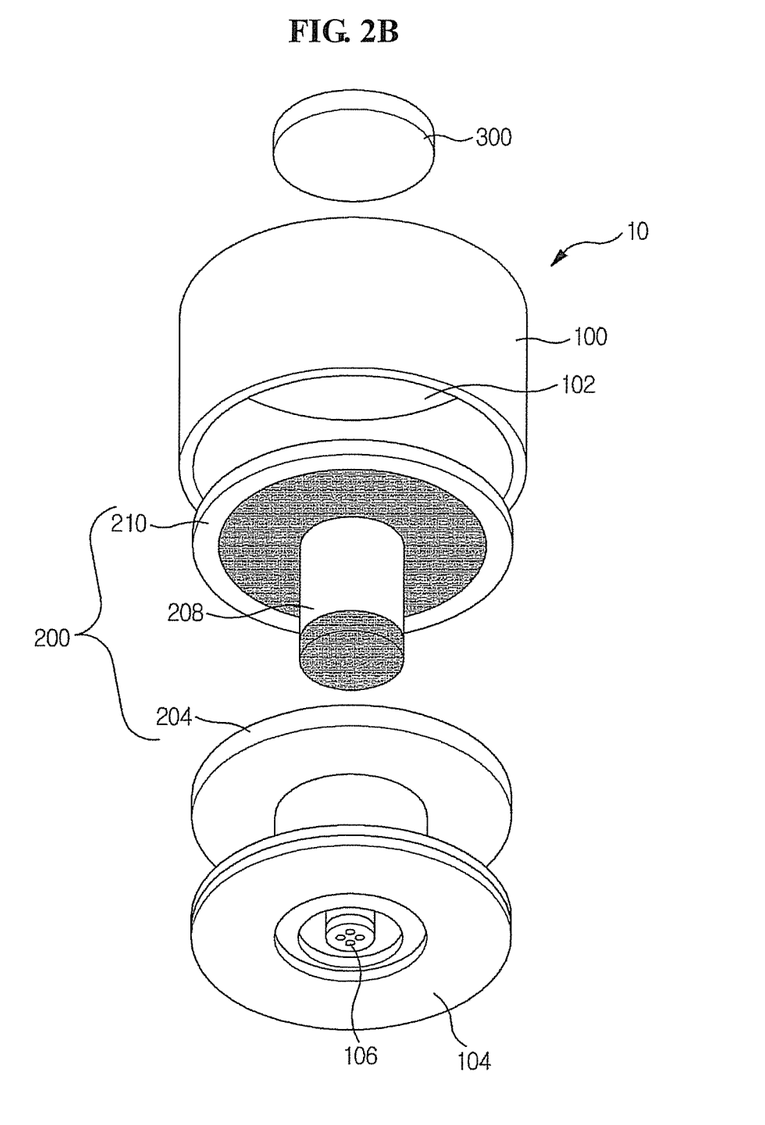
FIG. 2B is an exploded perspective view showing each element constituting a device according to one exemplary embodiment of the present disclosure.
Figure 2C:
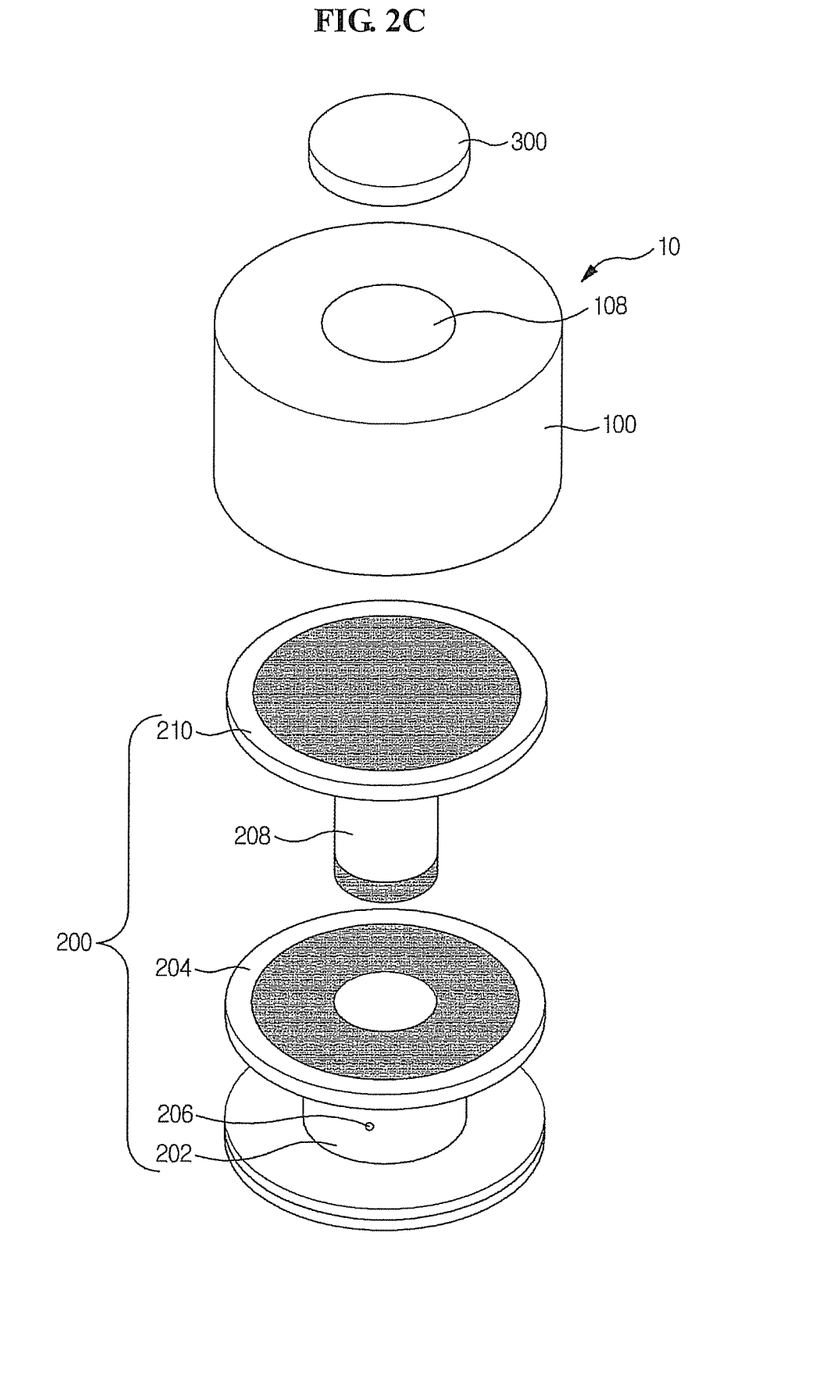
FIG. 2C is a further exploded perspective view showing each element constituting a device according to one exemplary embodiment of the present disclosure.

As shown in FIGS. 2A to 2C, the present device comprises a chamber 100 having a top end 102 and a bottom end 104, and the chamber 100 is provided with at least one outlet 106 formed on the bottom end 104 and a septum 108 formed on the top end 102. The bottom end 102 is a part where a drug is released through the outlet 106 formed thereon and injected into a site of interest.

The outlet 106 may come in various shapes and sizes and the numbers may be various and when a plurality of outlet is employed, they may take a variety of arrangement among them and in relation to the device. Also as described in hereinafter, the sizes and numbers of the outlet may be determined in consideration of the amount of a drug released per injection/actuation and/or the ratio of its total area to that of the inlet(s). For example, the present device may comprise from one to several outlets, for example 1 to 30, 1 to 20, 1 to 10, 1 to 5 or 1 to 3 outlets, but the number is not limited thereto. The inlet 206 may come in various shapes and sizes and the numbers may be various and when a plurality of outlet is employed, they may take a variety of arrangement among them and in relation to the device. Also as described in hereinafter, the sizes and numbers of the inlet may be determined in consideration of the amount of a drug released per injection/actuation and/or the ratio of its total area to that of the outlet(s). In one embodiment, the present device comprises 2 inlets.

By controlling the number and/or sizes of the outlet 106, the number of actuation, the size and/or number of the outlet, the ratio of the total area of the inlet and the outlet, or the volume of the cylinder or the combination thereof, the amount of a drug released using the present device is able to be regulated reproducibly and accurately.

Figure 4:
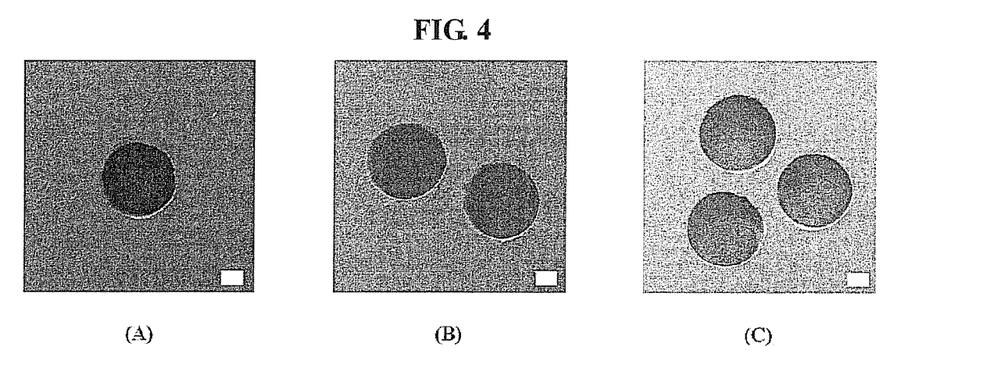
FIG. 4 is a scanning electron microscopic image of an outlet with 700 micrometer in diameter comprised in a device according to one exemplary embodiment of the present disclosure, wherein the scale bar represents 200 micrometer.
Figure 5A:
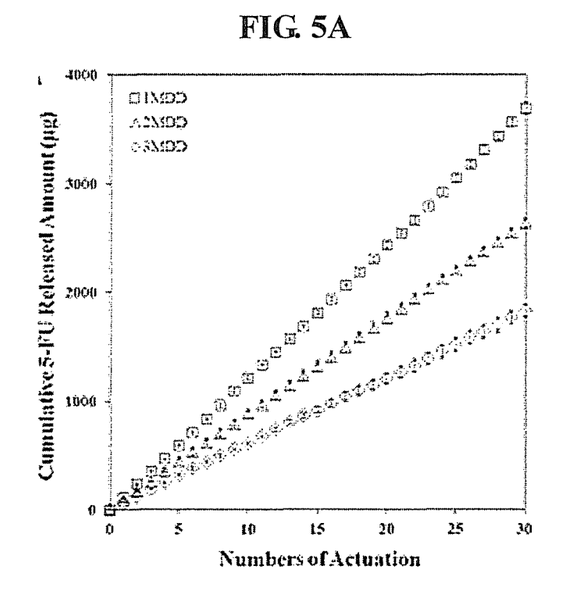
Figure 5B:
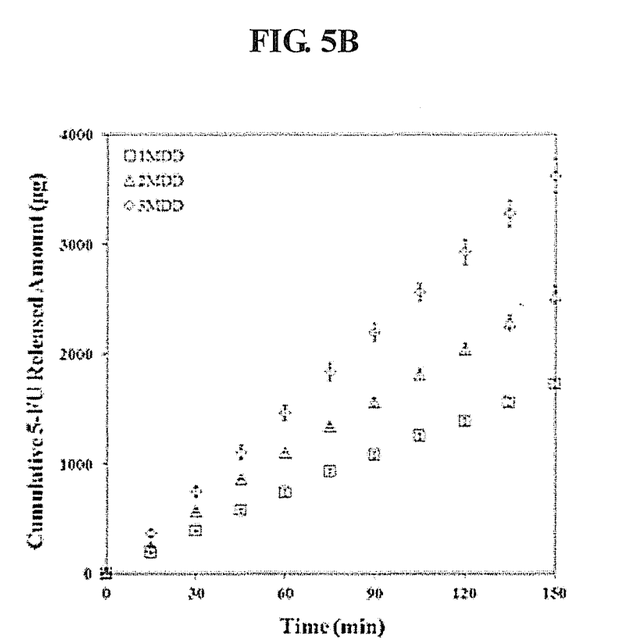
FIG. 5B is a graph showing the averaged amount of 5-FU released during the 3 consecutive actuations at different time points.
Figure 5C:
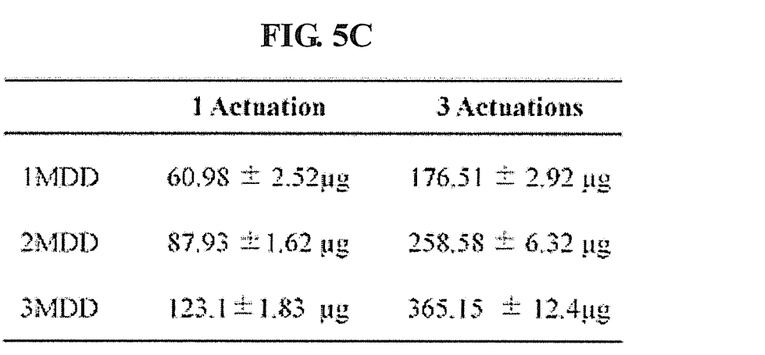
FIG. 5C is a table showing the mean value of 5A (left column) and 5B (right column).
Figure 6:
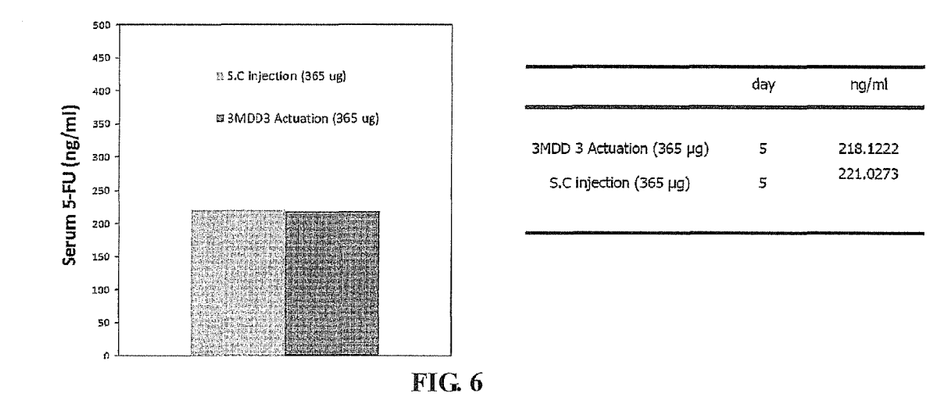
FIG. 6 is a result comparing a drug delivery in rats using a device according to one exemplary embodiment of the present disclosure with that using the conventional subcutaneous injection. The present device was implanted into the back of a rat followed by an application of magnetic field and the concentration of the drug in blood was measured. For the subcutaneous injection group, the same procedure was performed except that the drug was injected into the back of a rat. As a result, it was found that there were no differences in pharmacokinetics between the two groups. This indicates that the drug delivery using the present device is as effective as the conventional method and thus can be utilized usefully as an implantable drug delivery system.

FIG. 4 is a scanning electron microscopic image of an outlet with 700 micrometer in diameter and FIG. 5 is a result showing the delivery of 5-FU using one exemplary device of the present disclosure, in which (A) is a graph showing the accumulated amount of 5-FU released from a device with 1 (1 outlet) to 3 MDD (3 outlets) respectively with the increased number of actuations, (B) is a graph showing the averaged amount of 5-FU released during the 3 consecutive actuations at different time points, and (C) is a table showing the mean value of 5A (left column) and 5B (right column).

Referring to FIGS. 1, 4 and 5, in one embodiment of the present disclosure, the devices with 1 (1 MDD), 2 (2 MDD) or 3 (3 MDD) outlets, each having a diameter of 700 micrometer have been manufactured and the profile of drug release from each of the devices was examined. For this, each of the device manufactured was implanted in the back of a mouse and magnetic force of about 1800G, 1300G and 4000G (Magnet, M1, M2 and M3, respectively, refer to the description hereinafter) was applied. As a result, when the accumulated amount of drug released with increasing number of actuations was examined using M3 magnetic force, it was found that the amount of drug released per one injection or actuation was 60.98±2.52 µg for 1 MDD, 87.93±1.62 µg for 2 MDD and 123.1±1.83 µg for 3 MDD. This indicates that the amount of drug released is proportional to the number of outlets. Also to examine whether the amount of a drug released in the range that is therapeutically significant can be controlled, three consecutive injections or actuations were performed using each of the devices with 1MDD, 2MDD or 3MDD at each time point. As a result, it was found that the amount of drug released during three consecutive injections or actuations was 176.51±2.92 µg for 1 MDD, 258.58±6.32 µg for 2 MDD and 365.15±12.4 µg for 3MDD. This indicates that the amount of drug released can be reproducibly controlled. Based on the above results, a linear equation of y=31.5 x+27 where x represents the number of outlets, y represents the amount of drug released, can be derived. Using such calculated equation as described above, the amount of drug released per actuation with a certain number of outlets can be calculated and thus the amount of drug released can be controlled. In the experiment as described above, the amount of drug delivered was calculated to be about 60 µg for 1 MDD, about 90 µg for 2 MDD and about 120 µg for 3 MDD. The device manufactured and used for the experiments had a ratio of total area of the outlet to the inlet is 1:12 for the device with one outlet, 1:18 for the device with two outlets and 1:36 for the device with three outlets.

In one exemplary embodiment, the amount of drug released can also be reproducibly controlled by varying the number of actuations or injections and the number of outlets. Referring to A of FIG. 5, when three devices, each one with one, two or three outlets of 700 micrometer in diameter, respectively, were tested for the drug release with an increasing number of actuations, it was found that the amount of drug released per each actuation is reproducible. Also As shown in B of FIG. 5, when the amount of drug released during the three consecutive actuations was tested, it was found that the amount released is increased by 3 times compared to the amount released with one injection. These results indicate that the amount of drug released can be controlled either employing the number of outlets or the number of actuation or injection or both.

Referring to FIG. 2A and 2C, the present device is provided with an element, for example a septum 108 in one embodiment, for charging or recharging the device with a drug therethourgh. The septum 108 is formed on the top end 102 of the chamber 100 and the present device is implanted at a site of interest in such a way that the top end 102 is disposed facing the skin. The septum 108 is configured to be closed when not in use, and is only opened when it is used for charging or recharging a drug into the device, thus the chamber is practically sealed off from the outside. So, as long as fulfilling such functions, elements with various structures may be employed and in one embodiment, septum 108 is used.

Referring to FIG. 1B and FIG. 2A to 2C, a drug is released from the device by the motion exerted by an actuator 200, which is initiated by the application of an initiating magnetic force to the top end of the device. The actuator 200 comprises a cylinder 202 and a piston 208 that is located inside the cylinder and the piston 208 travels back and forth inside the cylinder. The cylinder 202 comprises at least one inlet 206 through which a drug is introduced inside of the cylinder from a drug reservoir 212.

In the present device which is operated by on-off manner as described above, the ratio of the total area of the outlet 106 to that of the inlet 206 is crucial for a proper operation of the present device. Without being limited by any theoretical explanation, this is thought to result from the negative pressure generated inside the cylinder 202 during the upward movement of the piston 208 comprised in actuation part 200 when the initiating magnetic field is applied using an external controller 300. Through this movement, a drug in the reservoir 212 is introduced inside of the cylinder 202 through the inlet 206. As such when the total area of the outlet 106 is same as or similar to that of the inlet 206, there is a possibility that a liquid such as bodily fluid may be introduced to the cylinder by the negative pressure generated in the cylinder. Therefore it is preferable that the negative pressure is applied only to the inlet 206. For example when at least one of the inlet 206 and the outlet 106 is employed for the present device, it is preferable that the total area of the inlet 206 is at least 10 times larger than that of the outlet 106. In one embodiment of the present disclosure, the ratio of the total area of the outlet to that of the inlet is above 1:1, about 1:50, particularly 1:40, particularly 1:30, particularly 1:20, more particularly about 1:10. However the ratio may be various depending on the thickness of the structures where the inlet and outlet are formed, or the other factors that described above in relation to the control of the amount of drug released. People skilled in the art would be able to select the appropriate ratio considering such variations. For example, in cases where the cylinder wall where the inlet is formed is thicker than that of the top end of the chamber where the outlet is formed, it is preferable that the total area of the inlet(s) is increased by a fold change in the thickness of the cylinder compared to the thickness of the top end. The thicker the cylinder wall is, the stronger the fluid resistance becomes. Thus it is preferable to keep the resistance of the inlet much lower than that of the outlet.

The cylinder 202 further comprises a first flange 204 protruding outwardly from an outer surface of the cylinder and is formed on one end of the cylinder that is closer to the top end of the chamber than the other end of the cylinder. The cylinder is formed along the outer circumference surface of the cylinder and is configured to abut the inner surface of the chamber to form a gap between the inner surface of the chamber and the outer surface of the flange 204. The size of the gap is not particularly limited as long as it has a size that is enough for allowing a drug to flow in one direction from the top end to the bottom end of the chamber in the space formed within the chamber. For example, the gap may be about 100 micrometer to 1 mm, but the gap is not limited thereto.

The piston 208 comprises an end cap 210. The end cap covers and thus is formed on one end of the piston that is closer to the top end of the chamber than the other end. The end cap 210 has a diameter that is same or different to that of the cylinder 202 and is configured to abut the inner surface of the chamber to form a gap between the inner surface of the chamber and the outer surface of the end cap 210. The gap is formed to have a size that is enough for allowing the piston 208 to move back and forth through the space or channel that is defined by the top end of the chamber and the end of the cylinder where the first flange is formed when the magnetic force applied or removed. Preferably the diameter of the end cap is larger than that of the piston. In this context the part of the end cap that is protruding outwardly from the piston may be referred to a second flange. For example, the gap may be about 100 micrometer to 1 mm, but the gap is not limited thereto.

The present device is provided with an external controller 300 for supplying an external magnetic force or an initiating magnetic force to the device. In the absence of the external magnetic force, the first flange 204 and the end cap 201 is positioned being closed to each other, and when the external magnetic field is applied, the piston 208 of the actuator 200 is pulled upward toward the top end of the chamber. For this, at least one of the first flange and the end cap is formed of a magnetic material or a material that is responsive to a magnetic force such that they adhere to each other when the initiating magnetic force is not applied. For example, when the first flange is made of a material such as magnet, the end cap is made of a material that is responsive to the magnetic force such as ferrite. Further the flange and the end cap can be made of a same or a different material.

The present device is provided with a drug reservoir 212. The drug reservoir 212 is formed in a space within the chamber 100 that is not occupied by the actuator 200. As described above, the present device delivers a drug to a site of interest in a manner that a drug introduced into the cylinder through the inlet which is opened by the application of the initiating magnetic force or the external force is discharged through the outlet formed on the bottom end of the chamber to the site of interest of the body where the device is implanted. To this end, when the first flange has a magnetic force M1 and the end cap has a magnetic force M2, and the initiating magnetic force is M3, the M1, M2 and M3 meet the following condition for the operation: M2−M3>M2−M1 for the introduction of the drug inside of the cylinder through the inlet; and M2−M3<M2−M1 for the release of a drug to a site of the body where the device is implanted through the outlet. As long as such condition is satisfied, magnetic force of M1, M2 or M3 with a variety of strength may be employed for the present device. In one embodiment of the present disclosure, the magnetic force of M1, M2 and M3 is about 1800G, 1300G and 4000G, respectively. The particular force of the magnetic field may be various depending on the size of the device, magnetic materials or materials that is responsive to the magnet used to manufacture the device. In one embodiment, the magnetic force is calculated by the following formula when designing a device:

$$F(x) = \frac{\pi * \mu 0}{4} * M^2 * R^4 * \left[ \frac{1}{x^2} + \frac{1}{(x+2h)^2} - \frac{2}{(x+h)^2} \right]$$

wherein:

$$\mu_0 = 4 * \pi * 10^{-7} (I*m/A)$$

$$B_0 = (\mu 0/2) * M \text{ magnetic flux density, in } T$$

$$R = \text{radius, in } m$$

$$X = \text{distance between two magnets, in } m$$

$$h = \text{thickness of magnet, in } m$$

Figure 3:
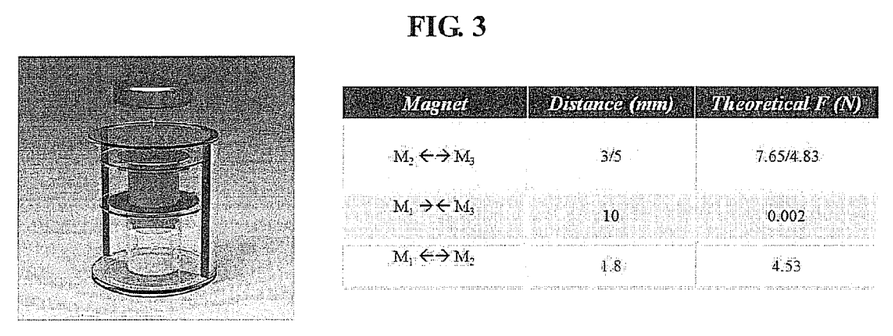
FIG. 3 is a schematic illustration of a device according to one exemplary embodiment of the present disclosure and a theoretical calculation of the magnetic forces involved the device, wherein the force is 1800G for M1, 1300G for M2 and 4000G for M3.

FIG. 3 is a schematic illustration of a device according to one exemplary embodiment of the present disclosure and a theoretical calculation of the magnetic forces involved the device, wherein the force is 1800G for M1, 1300G for M2 and 4000G for M3.

Referring to FIG. 3, the time that takes the piston to move up by the application of an external magnetic force and to move down back to its original position, namely the time during which the outlet(s) is opened is able to be controlled by the magnetic force of M1, M2 and/or M3, particularly M3. The amount of time as described above may be determined considering the amount of a drug administered, the concentration of a drug, the number of the outlet. In one embodiment, the outlet is opened for about 1 sec or less.

As such, the amount of a drug administered can be finely controlled as required using the present implantable device. Also the implanted device may be used for semi-permanently by recharging a drug through the septum formed on the device.

The present device is used implanted on animals, particularly mammals, and thus the device is manufactured to a size that is appropriate for the subject that requires an implant of the device. The device is made of a material that is biocompatible and chemically inert. In particular, the actuator 200 is preferable to be made of or coated with a material that is resistant to degradation by contact with a liquid or a drug, and that is not reactive to a drug. For example the material includes a chemically inert and biocompatible water resistance materials, for example such as PEEK(Polyether Ether Ketone), Polyimide, LCP (Liquid Cristal Polymer), PDMS (Polydimethylsiloxane), Polyurethane, Titanium and Stainless-Steel. In one embodiment, all or at least part of the actuator, particularly the part that is made of magnetic material is coated with water resistant material. The external controller is preferably made of a material having magnetic force, i.e., magnet.

The present device is made to proper sizes and shapes considering the types or kinds of a site of the body the device is implanted, the kinds of animals, the amount of a drug required to be kept in the device and/or the amount of time the device is required to be implanted and the like. Referring to FIG. 1, the device is roundly shaped and has dimension of 20 mm in diameter and about 14 mm in height, where the cylinder has a dimension of about 8 mm in diameter and about 7 mm in height; and the piston has a dimension of about 4 mm in diameter and about 8 mm in height, and the inlet has a diameter of about 3 mm.

As described above, the present device can be conveniently used for drug delivery as implanted systems for treating chronic disease, condition or state that requires medication therapy over extended period of time, for example cancer, diabetes, chronic pain, AIDS and contraception and the like. So the drugs which may be delivered by the present device include any material with therapeutic and/or preventive effect or prodrugs thereof and a combination thereof. The drugs may also be formulated as a fast acting or as a sustained release and may also include pharmaceutically acceptable carriers, excipient, and/or agents The present device can be used implanted in various animals for example in various sites of interest of the body. The site includes those that requires a direct treatment or those from which the drug delivered is transferred to a site where the activity of drug is required. The device may be implanted intramuscularly or subcutaneously and the proper site for implant includes the abdomen, the back of the arm or the interior of an organ, without being limited thereto.

While the present device has been shown and described in terms of various aspects, it will be apparent to those skilled in the art that various modification and changes may be made without departing the principles and spirit of the invention. Thus the scope of the invention must be defined by the appended claims and their equivalents.

With respect to the use of substantially any plural and/or singular terms herein, those having skill in the art can translate from the plural to the singular and/or form the singular to the plural as is appropriate to the context and/or application. The various singular/plural permutations may be expressly set forth herein for sake of clarity.

DESCRIPTION OF REFERENCE NUMERALS

10: a device
100: a chamber
102: a top end of the chamber
104: a bottom end of the chamber
106: an outlet
108: a septum for charging or recharging drug
200: an actuator
202: a cylinder
204: a flange
206: an inlet
208: a piston
210: an end cap
212: a drug reservoir
300: an external controller

What is claimed is:

1. A device for drug delivery using a magnetic force, the device comprising:
    a chamber comprising a top end and a bottom end;
    the chamber further comprising at least one septum for charging a drug into the device and at least one outlet for discharging a drug from the device, each being formed on a top end and a bottom end of the chamber, respectively;
    an actuator located inside the chamber,
    the actuator comprising a cylinder and a piston;
    the cylinder comprising at least one inlets formed on a side thereof and a first flange protruding outwardly from an outer surface of the cylinder;

the first flange formed on an end of the cylinder that is closer to the top end of the chamber and configured to abut an inner surface of the chamber;

the piston located inside the cylinder and comprising an end cap;

the end cap covering an end of the piston that is closer to the top end of the chamber such that the end cap is interposed between the first flange and the top end of the chamber and configured to abut the inner surface of the chamber;

a drug reservoir formed in a space within the chamber that is not occupied by the actuator; and an external controller for supplying an initiating magnetic force to the device, wherein at least one of the first flange and the end cap is formed of a magnetic material or a material that is responsive to a magnetic force such that they abut to each other when the initiating magnetic force is not applied.

2. The device of claim 1, wherein an operation of the device is initiated by applying the initiating magnetic force M3 to the top end of the chamber, thus pulling the piston upward and opening the inlet through which a drug is introduced inside of the cylinder followed by a subsequent release of the drug through the outlet and the drug is delivered to a site of a body where the device is implanted, wherein the first flange has a magnetic force M1 and the end cap has a magnetic force M2, and the M1, M2 and M3 meet the following condition for the operation: M2−M3>M2−M1 for the introduction of the drug inside of the cylinder through the inlet; and M2−M3<M2−M1 for release of the drug to the site of the body where the device is implanted through the outlet.

3. The device of claim 1, wherein a ratio of a total area of the outlet to that of the inlet is above 1:1.

4. The device of claim 1, wherein an amount of a drug released from the drug reservoir per actuation is controlled by a size and/or number of the outlet, a ratio of a total area of the inlet and the outlet, or a volume of the cylinder or a combination thereof.

5. The device of claim 1, wherein the external controller has a magnetic force that meets the following condition: M2−M3>M2−M1 for the introduction of a drug inside of the cylinder through the inlet; and M2−M3<M2−M1 for release of the drug through the outlet into a site of a body where the device is implanted, wherein M1, M2 and M3 are as defined in claim 2.

6. The device of claim 1, wherein a number of the outlet formed is between 1 and 30.

7. A method of delivering a drug to a subject, comprising: providing the device of claim 1, implementing the device at a site of interest of a subject and actuating the device to deliver the drug in an amount sufficient to treat a disease of interest or relieve a symptom of interest.

* * * * *